United States Patent [19]

Tomko

[11] Patent Number: 4,876,725
[45] Date of Patent: Oct. 24, 1989

[54] METHOD AND APPARATUS FOR FINGERPRINT VERIFICATION

[75] Inventor: George J. Tomko, Toronto, Canada

[73] Assignee: Mytec Technologies Inc., Toronto, Canada

[21] Appl. No.: 105,615

[22] Filed: Oct. 8, 1987

[51] Int. Cl.⁴ .............................................. G06K 9/00
[52] U.S. Cl. .......................................... 382/4; 382/2; 382/31; 356/71; 350/376; 350/162.12
[58] Field of Search ...................... 356/71; 382/2, 4, 5, 382/31; 350/162.12, 162.13, 3.72, 3.76; 364/713, 837

[56] References Cited

U.S. PATENT DOCUMENTS

| | | | |
|---|---|---|---|
| 3,511,571 | 5/1970 | Ogle | 356/71 |
| 3,532,426 | 10/1970 | Lemmond | 356/71 |
| 3,704,949 | 12/1972 | Thomas | 356/71 |
| 3,716,301 | 2/1973 | Caulfield | 356/71 |
| 3,743,421 | 7/1973 | Maloney | 356/71 |
| 3,781,113 | 12/1973 | Thomas | 356/71 |
| 3,807,829 | 4/1974 | Close | 350/3.72 |
| 3,873,970 | 3/1975 | McMahon | 382/4 |
| 3,891,968 | 5/1975 | McMahon | 356/71 |
| 3,944,978 | 3/1976 | Jensen | 356/71 |
| 4,053,228 | 10/1977 | Schiller | 356/71 |
| 4,206,965 | 6/1980 | McGrew | 350/3.76 |
| 4,357,597 | 11/1982 | Butler | 382/2 |
| 4,641,350 | 2/1987 | Bunn | 356/71 |
| 4,764,889 | 8/1988 | Hinton et al. | 364/837 |

Primary Examiner—Leo H. Boudreau
Assistant Examiner—Jose L. Couso
Attorney, Agent, or Firm—Ronald D. Faggetter

[57] ABSTRACT

The invention relates to an optical processing fingerprint verification device. A light source illuminates a prism upon which the user has placed two fingers to that light reflected from the prism is modulated by the data of the users fingerprints. The fingerprint data beam passes through a lens and undergoes a Fourier transform at a card including a reflection hologram matched to two fingerprints of a reference individual. The intensity distribution of the ligh reflected from the hologram determines whether a match exists. Use of a reflection hologram allows use of an incoherent light source. The two fingers are located on the prism by movable guides positioned by information on the card as to the relative length and the width of the two fingers of the reference individual. This provides a second level of verification. Scaling sensitivity may be reduced by utilizing a frequency multiplexed hologram.

11 Claims, 2 Drawing Sheets

METHOD AND APPARATUS FOR FINGERPRINT VERIFICATION

BACKGROUND OF THE INVENTION

This invention relates to a method and apparatus for fingerprint verification and more particularly to apparatus for recording a reflection hologram of fingerprint data and to a method and apparatus for optically filtering input fingerprint data with the hologram to form a correlation signal.

It is common to purchase goods and services and obtain cash from Automatic Teller Machines (ATMs) through the use of credit or bank cards. Currently, over 900 million plastic magnetic stripe credit and debit cards are circulating in North America and there is no reliable method to verify that the card user is the legal user. The Personal Identification Number (PIN) in the case of ATM access, or the signature on the invoice form which the card user signs does not constitute nor ensure positive identification. Signatures can be falsified and PINs can be surreptitiously obtained.

The credit card industry in the United States transacted about $350 billion in charge volume in 1986 and the concomitant losses due to fraud was close to $750 million. Stolen cards make up 21 percent of this loss for a total of $150 million. It is known that federal police forces have become deeply involved in trying to stop interstate and even intercontinental schemes to defraud thousands of credit card holders. These developments place existing credit cards in a position of not just having occasional security problems, but of being susceptible to broadscale criminal activities with little or no protection.

Incorporation of a photograph of the legal user on the card is another method used with charge cards; this method is also used with passports. However, this method also does not allow for positive identification. When a system relies on the human element of a guard service, for example, visual identification of an individual by a photograph on an ID card can be impaired by personal stress, fatigue, outside disturbances, or just sheer numbers of people seeking entry. Furthermore, appearances can be altered to match the photo on the card and cards can be forged with the photo of an illegal user.

Overall, signatures, PINs and photographs have served as imperfect parameters for card user verification. Moreover, the fraudulent use of cards will cost companies in North America in excess of one billion dollars in the next year.

With the rising cost of fraud the use of fingerprints as a verification parameter has been explored. Fingerprints are unique to each individual and thereby constitute positive verification.

Optical processing techniques using holographic matched filters have been a major conceptual advance in the fingerprint identification area. Optical processing methods differ fundamentally from digital techniques in that the reference information is manipulated not in the image plane, but in the Fourier transform plane normally formed by a lens. Verification is accomplished by superimposing the "live" fingerprint after Fourier transformation onto the transformed reference fingerprints. This procedure achieves a correlation between the two sets of fingerprint patterns, the result of which is a focused beam of light if a match occurs. This technique is a real time parallel processing method which allows the verification cycle to be completed within a second or so (the time from placement of the user's fingerprint on the read lens to a "match" or "no-match" identification).

Theoretically, more accurate verification can be obtained with optical processing. Fingerprint patterns are susceptible to degradation and damage because of the wear and tear of everyday activity such as cuts, abrasions and foreign contaminants. The wear and tear contributes "noise" to the comparison system and if not compensated will lead to higher false positive and false negative verifications. To compensate for "fingerprint noise" with digital techniques in the real time domain is a complex and expensive process since an algorithm using serial processing would have to be used. In the frequency transform domain, though, the removal of "fingerprint noise" is inherent in the comparison process. Since comparison is accomplished using a holographic matched filter, the matched filter removes all spatial frequencies which are not within the band comprising the reference fingerprint. This turns out to be a major portion of the "noise" spectrum. Furthermore, by the use of an appropriate high pass spatial filter, undesired low frequencies and dc biases can be removed to improve the correlation accuracy. Accordingly, optical processing can lead to lower false positive and false negative verification.

Methods to identify fingerprints using Fourier transform holograms and optical correlation techniques have been described in the art. The practicalities, however, associated with building such devices have been disappointing. Devices have been expensive, complex and unreliable thereby precluding their widespread use in the commercial marketplace.

To date, the methods suffer from a number of disadvantages, foremost among which is a high degree of inaccuracy in a real world environment. For example, mismatch can occur because of rotational misalignment and/or scale changes between the image and hologram. This can result from a slight rotational movement of the finger in the identification device or inconsistent optics between the device that records the hologram and that which identifies the card user. Scale changes also result if the user's fingerprints enlarge as may occur with swelling or obesity. A decrease in the signal-to-noise ratio of the system by a factor of 500 results from only a 3.5 degree change in rotation or a 2 percent change in scale between the "live" and reference fingerprint patterns.

Prior art devices also are dependent on the use of coherent light sources during both the recording and identification cycle which increases the expense and complexity of the devices. Sensitivity is a further problem. The optical system must have positional stability to maintain a high signal-to-noise ratio and can be severely disturbed by a slight vibration which can knock an optical element out of position.

Another difficulty as illustrated by U.S. Pat. No. 3,781,113 to Thomas issued Dec. 25, 1973 and U.S. Pat. No. 3,704,949 to Thomas et al. issued Dec. 5, 1972 is the cumbersome method of measuring the correlation signal. In both of these patents a motorized reticle is used to chop the light in order to distinguish between focused (correlated) and unfocused (uncorrelated) light.

SUMMARY OF THE INVENTION

I have found that one or more of the disadvantages of the prior art fingerprint verification techniques may be overcome by an optical processor fingerprint verification device comprising a source of incoherent light for providing an illuminating beam along a beam path; input means including means to receive at least one fingerprint or fingerprint recording of an individual located in said beam path for producing an optical information beam modulated with data from said at least one fingerprint or fingerprint recording along an optical information beam path; optical Fourier transform means in said optical information beam path for providing a Fourier transformed optical information beam in a transform plane; supporting means for supporting a reference data record including a pre-recorded reflection hologram of at least one reference fingerprint in said transform plane, said pre-recorded reflection hologram for reflecting and filtering a Fourier transformed optical information beam to provide light having an intensity distribution representing the correlation between said pre-recorded reflection hologram and said Fourier transformed optical information beam; verification indicating means responsive to the intensity distribution of light reflected from said pre-recorded reflection hologram when said pre-recorded reflection hologram is illuminated by a Fourier transformed optical information beam.

A reflection hologram allows the use of a non-coherent white light source which is less expensive and less sensitive than a coherent source such as a laser.

Preferably, the user initiates comparison by inserting two adjacent fingers into finger positioning apparatus comprising moveable guides which have been positioned so that the prints of the legal user will be located directly over a read prism without rotation. The finger position apparatus also provides another dimension of verification to the system as an improper user, with different relative finger positions and widths, would have his fingers improperly positioned.

Preferably too, the hologram is frequency multiplexed in order to minimize scale change errors.

In another embodiment, the present invention comprises a method of fingerprint verification comprising illuminating an input means upon which at least one fingerprint has been placed with a beam of incoherent light whereupon incidence of said beam on said at least one fingerprint causes a fingerprint data beam to be produced; passing said fingerprint data beam through an optical Fourier transform means; filtering the Fourier transform of said fingerprint data beam with a pre-recorded reflection hologram of a Fourier transform of at least one reference fingerprint to provide reflected light having an intensity distribution representing the correlation between said Fourier transform of said fingerprint beam and said pre-recorded reflection hologram; indicating a match or a mismatch between said at least one fingerprint and said at least one reference fingerprint in response to the intensity distribution of light reflected from said reflection hologram.

In yet another embodiment, the present invention comprises a device to produce a reference data record for use in connection with a fingerprint verification apparatus comprising: a source of coherent light to provide an illuminating beam along a beampath and a reference beam along a reference beam path; input means including means to receive at least one fingerprint or fingerprint recording of an individual in said beam path for producing an optical information beam modulated with data from said at least one fingerprint or fingerprint recording along an optical information beam path; optical Fourier transform means in said optical information beam path for providing a Fourier transformed optical information beam in a transform plane; supporting means for locating recording media both in said transform plane and in said reference beam path; reflection hologram processing means for processing a reflection hologram onto said recording media thereby forming a reference data record.

BRIEF DESCRIPTION OF THE DRAWINGS

In the drawings which illustrate embodiments of the invention.

DETAILED DESCRIPTION OF THE PREFERRED EMBODIMENTS

Figure 1:
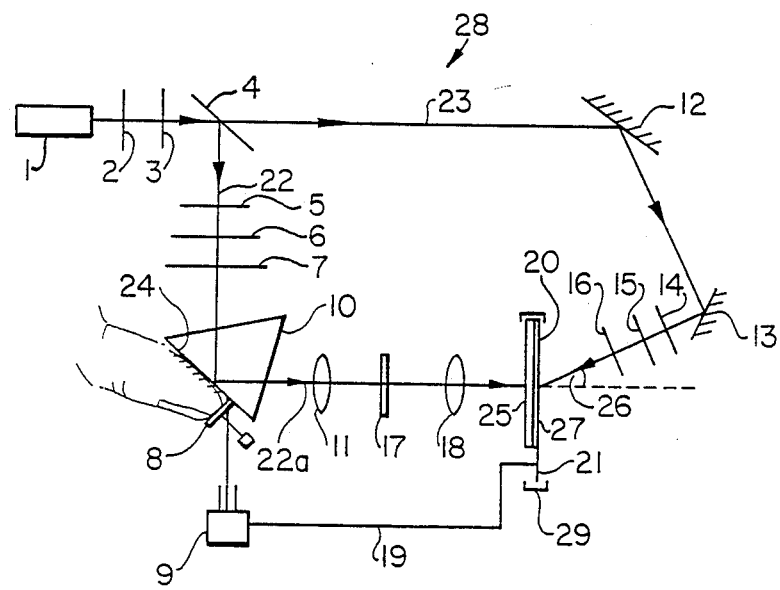
FIG. 1 is a schematic view of a system for encoding fingerprint information.

Referring to FIG. 1, the system for encoding fingerprint information comprises an encoding device indicated generally at 28 and a card 20. Card 20 may be a charge card or a passport. The device 28 comprises a coherent, variable wavelength, light source 1 which directs a light beam through variable attenuator 2 and shutter 3 to variable beam splitter 4. The beam splitter splits the beam into two beams, 22 and 23. Beam 22 passes through objective lens 5, pinhole spatial filter 6 and collimating lens 7. The beam 22 then enters prism 10 which has a refractive index such that in the presence of air at face 24 of the prism, the beam 22 undergoes total reflection.

Face 24 is located in the front focal plane of lens 11. Spatial noise filter 17 is located in the back focal plane of lens 11. The reflected beam 22a passes through lens 11, spatial noise filter 17, and collimating lens 18, thence it impinges on a device 25 to process a reflection hologram onto recording medium 27 of card 20 which has been previously inserted into supporting means 29 of the encoding device.

Beam 23 is reflected by mirrors 12 and 13 through objective lens 14, pinhole spatial filter 15, and collimating lens 16 to the opposite side of recording medium 27 to that of beam 22a such that beam 23 makes an angle 26 with beam 22a at the recording medium.

The apparatus is configured such that the total path lengths of the two beams are equivalent.

A finger position indicator, more fully described hereinafter in connection with FIG. 3, comprises guides 8 located over face 24 of the prism. The position of the guides is selectively converted to an analog electrical signal which is passed to A/D converter 9. The output digital signal passes through electrical leads 19 to magnetic stripe 21 on card 20.

Figure 3A:
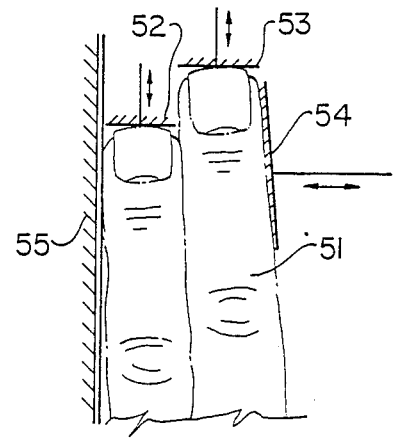
FIGS. 3A and 3B are schematic views of the guides of a finger position indicator.
Figure 3B:
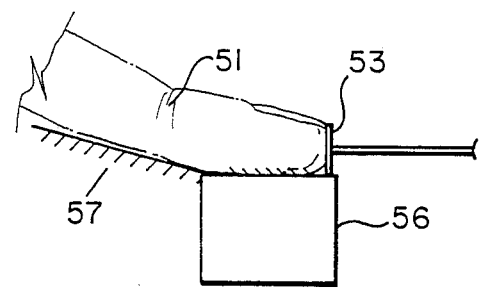

In operation of the encoding system, two adjacent fingers of the legal user are placed correctly over the read prism 10 and the guides 8 are positioned to secure a snug fit around three sides of the fingers taking into account the different lengths of the fingers (see FIG. 3). An analog position signal from the guides is converted to a digital signal by an analog-to-digital converter 9 and passed on to the card 20 by electrical leads 19, where it is stored on the magnetic stripe 21 (or semiconductor memory) of the card.

A wavelength is then selected for light source 1 and the source is activated. Shutter 3 is then opened so that the beam from source 1 is split in two by variable beam splitter 4. The aforedescribed objective lens and pinhole spatial filter in the path of each beam (referenced at 5,6 and 14,15) serve to remove noise. The aforedescribed collimating lens (referenced at 7 and 16, respectively) through which each beam then passes serves to produce very uniform plane waves with less than about 5% spatial intensity variation.

Beam 22 then passes to prism 10. The refractive index of the prism is chosen so that the critical condition of total reflection at surface 24 is just achieved for the combination glass and air. Thus the total reflection condition strongly depends upon the refractive index of the media adjacent surface 24. Hence when the fingers of the legal user are impressed upon face 24 of the prism operating at the threshold of the critical index of reflection, the total reflection condition is destroyed at those regions at which the ridges of the fingerprints touch surface 24, but is maintained where the troughs of the fingerprints are spaced from the surface. Consequently, after reflection, beam 22a forms an information signal comprising the fingerprint pattern of the legal user. Since surface 24 of the prism is positioned at the front focal plane of lens 11 and spatial noise filter 17 is at the back focal plane of this lens, a spatial Fourier transform of beam 22a is formed at filter 17.

Filter 17 removes spatial frequency components above and below the range of human fingerprint patterns and unwanted low frequency components. This, in effect, removes part of the finger print noise from cuts, abrasions and foreign contaminants. Collimating lens 18 is placed behind the filter at 17 to maintain focus of the spatial transform. The device 25 to process a reflection hologram onto card 20 records the interference of the Fourier spatial transform of the fingerprint pattern and the reference beam at angle 26. The above process is carried out in stepped sequence for a series of wavelengths $\beta(1)$. -- $\beta(n)$, chosen appropriately to minimize errors due to scale changes. Scale changes up to $\beta(1)/\beta(n)$ (where $\beta(1) > \beta(n)$) will be compensated where both $\beta(1)$ and $\beta(n)$ are well within the spectrum of the white light source 31 referred to in FIG. 2. The recording medium 27 which resides on a flexible substrate is exposed at each step to the interference pattern by a step and repeat process with a holographic camera. After the last step, the recording medium has become an encoded plate which is a frequency multiplexed Fourier transform reflection hologram. The encoded plate is then glued or sandwiched into the card. The chosen angle 26 is a function of the optical resolution of the reflection hologram's processing method. The poorer the resolution of the method, the smaller the angle. However, angle 26 should be sufficient to ensure angular separation of the "cross-correlation" signal 50b from other optical signals in the fingerprint comparing system of FIG. 2.

The encoded plate and stored information relating to finger width and relative finger position comprise a reference data record.

Figure 2:
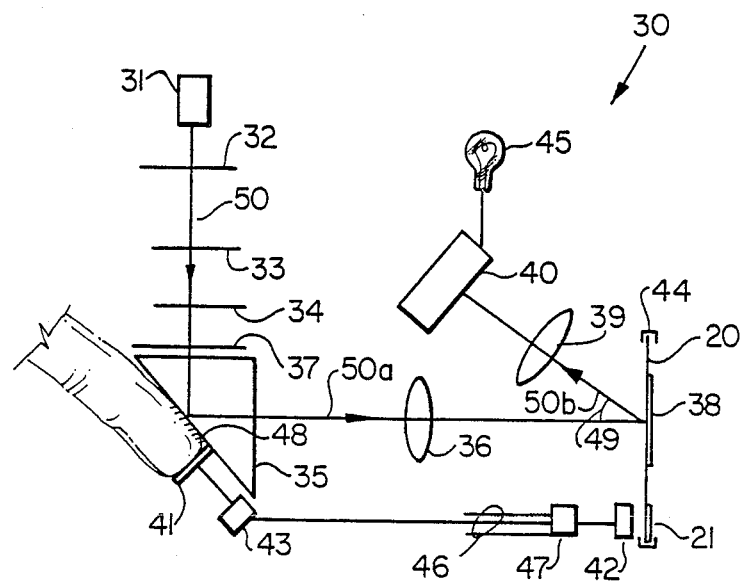
FIG. 2 is a schematic view of a system for comparing a reference data record with actual fingerprints.

Referring now to FIG. 2, the system for comparing a reference data record with an actual fingerprint comprises a comparison device indicated generally at 30 and a card 20. The device 30 comprises a non-coherent white light source 31 which directs a beam of light through objective lens 32, pinhole spatial filter 33, collimating lens 34 and diffraction grating 37 to read prism 35. Read prism 35 has an index of refraction such that, in the presence of air at face 48 of the prism, beam 50 undergoes total reflection. Prism 35 is positioned in the front focal plane of lens 36. Reflected beam 50a passes through lens 36 to encoded plate 38 on card 20 positioned in the back focal plane of lens 36 by positioner 44. Beam 50a is reflected from the encoded plate 38 at angle 49 (which is equivalent to the angle 26 of FIG. 1) through imaging lens 39 to matrix photo-threshold analyser 40. The photo-threshold analyser is electrically connected to light 45.

A magnetic stripe reader 42 is positioned adjacent magnetic stripe 21 of card 20. The magnetic stripe reader is electrically connected to digital/analog converter 47. Leads 46 leaving the digital/analog converter are connected to a series of motors and gears 43. Motors and gears 43 are mechanically interconnected to finger positioning guides 41 which are part of a finger position indicator more fully described hereinafter in connection with FIG. 3.

In operation, card 20 is inserted into positioner 44. Positional information for guides 41 is then read from the card and the guides are positioned appropriately. More specifically, magnetic stripe 21 of the card is read by the reader 42 and the digital information used to position guides 41 by means of a digital-to-analog converter 47, electrical leads 46, and a series of motors and gears 43.

The appropriate fingers of the user are then placed within the guides on the face 48 of the read prism 35. The non-coherent white light source 31 is activated and beam 50 therefrom passed through objective lens 32 and pinhole spatial filter 33 which remove noise from the beam. The beam 50 is then collimated by lens 34 and passed through a two dimensional diffraction grating 37 to prism 35. In a manner similar to that described in connection with the prism 10 of FIG. 1, the refractive index of prism 35 is chosen so that reflected beam 50a forms an information signal comprising the fingerprint pattern of the user. As face 48 of prism 35 is at the front focal plane of lens 36, a Fourier transform of beam 50a is formed at the back focal plane of lens 36 where encoded plate 38, which is a reflection hologram, is located. A fingerprint comparison is achieved by determining the correlation between the prints at the face of prism 35 and the holographically encoded reference prints. As the Fourier transform reflection hologram is a filter matched to the prints of the legal user, the correlation is achieved by reflecting beam 50a, which is the Fourier transform of the prints at the face of prism 35, from the hologram 38 on card 20. Thus, in the transform domain, the correlation is inherent in reflecting the Fourier transform of the fingerprints at prism 35 off the hologram on the card. The reflected beam 50b is then passed though an imaging lens 39 and sent to a matrix photo-threshold analyser 40. If the users fingerprints match the reference prints of the hologram a focussed bright spot will appear at the matrix photo-threshold analyser 40. Mismatches are indicated by a diffuse light at analyser 40. If the magnitude of the cross-correlation exceeds a preset value then a verification is obtained. This is indicated by such means as turning on light 45.

The comparison device may be made with injection moulding techniques whereby all the optical elements which are susceptible to movement or vibration are secured in a single mould. Moreover, a mould will ensure that all comparison devices will have consistent optics and thereby alleviate the potential of scale changes between the encoding and comparison devices.

FIG. 3 illustrates the guides of the finger position indicator for both the encoding system of FIG. 1 and the comparison system of FIG. 2. Two adjacent fingers 51 are placed flush with rigid guide 55. The fingers are positioned over the "read" prism 56 and on a slightly sloped support 57. In the encoding system, finger length guides 52 and 53 are then moved to fit snugly against the tips of the fingers. The finger width guide 54 is next moved to fit snugly against the right side of the rightmost finger. This position information is then sent to and recorded on the magnetic stripe of the card 20 employed with the system. In the comparison system, information from the card's magnetic stripe is used to position guides 52, 53 and 54 prior to placement of the fingers 51.

To understand why the finger position indicator improves verification it must be realised that all fingerprint verification systems are susceptible to some degree of error. For example, there is a certain probability that verifying a cardholder based on one fingerprint can result in a false positive identification since the system's resolution may not discriminate between two similar fingerprints from different individuals. Using prints from two fingers would decrease the false positive error but conversely could lead to an increased false negative errors if the same threshold parameters are maintained. Lowering the threshold would decrease false negatives but unless another comparison parameter were also used this would again increase false positive errors and negate the reason for using two fingerprints.

Fingershape geometry is a nearly unique variable amongst individuals and if used in conjunction with two fingerprints it can both improve verification and allow the threshold for fingerprint correlation to be relaxed in order to decrease false negative errors. For example, if the probability of two people having similar fingerprints within a preset threshold criteria is P(a), and of any two people having similar fingershape of two adjacent fingers is P(b), then the probability of two people having both similar fingerprints and similar fingershape is the product P(a)*P(b); i.e., the probability is decreased by at least an order of magnitude. Therefore, a higher probability exists that two people not discriminated by fingerprints would be discriminated by their fingershape.

In the present invention, an indication of fingershape is given by the relative position of the two fingerprints and the width of the two fingers.

Turning again to FIG. 2, in operation of the comparison system, if the card user were not the legal user, the guides 41 would most likely locate his two adjacent fingerprints on different areas of the "read" prism 35 from the areas on which the prints of the legal user would be located. The probability would therefore be high that either different areas of the illegal users fingerprints would be read, since the aperture of the "read" prism is limited, or the relative position of his fingerprints would be different to that of the legal user. In both cases, the Fourier transform would exhibit a different pattern than that of the reflection hologram 38 on card 20 and a match would not occur.

In place of the prism of FIGS. 1 and 2, a plate on which a record of the user's fingerprints has been made may be used as the input means by positioning same between the illuminating beam and the Fourier transform lens, in the front focal plane of the lens.

Where card 20 is a passport, the card may include a memory to record personal information and port of entry information now normally recorded by means of a stamp.

What I claim as my invention is:

1. An optical processor fingerprint verification apparatus comprising:
   (a) a source of incoherent light for providing an illuminating beam along a beam path;
   (b) input means including means to receive at least one fingerprint or fingerprint recording of an individual located in said beam path for producing an optical information beam modulated with data from said at least one fingerprint or fingerprint recording along an optical information beam path;
   (c) optical Fourier transform means in said optical information beam path for providing a Fourier transformed optical information beam in a transform plane;
   (d) supporting means for supporting a reference data record including a pre-recorded reflection hologram of at least one reference fingerprint in said transform plane, said pre-recorded reflection hologram for reflecting and filtering a Fourier transformed optical information beam to provide light having an intensity distribution representing the correlation between said pre-recorded reflection hologram and said Fourier transformed optical information beam; and
   (e) verification indicating means responsive to the intensity distribution of light reflected from said pre-recorded reflection hologram when said pre-recorded reflection hologram is illuminated by a Fourier transformed optical information beam.

2. The apparatus of claim 1 wherein said reference data record includes a pre-recorded reflection hologram of at least two reference fingerprints from two adjacent reference fingers and data representing the width and relative position of said at least two adjacent reference fingers and wherein said input means includes movable means positionable in response to said data representing the width and relative position of said at least two adjacent reference fingers for positioning said at least one fingerprint or fingerprint recording at said input means.

3. The apparatus of claim 1 wherein said pre-recorded reflection hologram is a frequency multiplexed pre-recorded reflection hologram, each frequency being within the spectrum of said source of incoherent light whereby the sensitivity of said fingerprint verification apparatus to scale changes in said at least one reference fingerprint is reduced.

4. The apparatus of claim 2 wherein said pre-recorded reflection hologram is a frequency multiplexed pre-recorded reflection hologram, each frequency being within the spectrum of said source of incoherent light whereby the sensitivity of said fingerprint verification apparatus to scale changes in said at least one reference fingerprint is reduced.

5. A device to produce a reference data record for use in connection with a fingerprint verification apparatus of the type described in claim 1 comprising:
   (a) a source of coherent light to provide an illuminating beam along a beam path and a reference beam along a reference beam path;
   (b) input means including means to receive at least one fingerprint or fingerprint recording of an individual in said beam path for producing an optical information beam modulated with data from said at least one fingerprint or fingerprint recording along an optical information beam path;

(c) optical Fourier transform means in said optical information beam path for providing a Fourier transformed optical information beam in a transform plane;

(d) supporting means for locating recording media both in said transform plane and in said reference beam path; and (e) reflection hologram processing means for processing a reflection hologram onto said recording media thereby forming a reference data record.

6. The apparatus of claim 5 wherein said input means includes means positionable by at least two adjacent fingers of said individual for providing position signals, said recording media includes a memory and means are provided to encode said position signals in said memory.

7. A method of fingerprint verification comprising:

(a) illuminating an input means upon which at least one fingerprint has been placed with a beam of incoherent light whereupon incidence of said beam on said at least one fingerprint causes a fingerprint data beam to be produced;

(b) passing said fingerprint data beam through an optical Fourier transform means;

(c) filtering the Fourier transform of said fingerprint data beam with a pre-recorded reflection hologram of a Fourier transform of at least one reference fingerprint to provide reflected light having an intensity distribution representing the correlation between said Fourier transform of said fingerprint beam and said pre-recorded reflection hologram;

(d) indicating a match or a mismatch between said at least one fingerprint and said at least one reference fingerprint in response to the intensity distribution of light reflected from said reflection hologram.

8. The apparatus of claim 5 wherein said source of coherent light is of a selectable wavelength and said reflection hologram processing means is for processing frequency multiplexed reflection holograms on said recording media.

9. The apparatus of claim 8 wherein said input means includes means positionable by at least two adjacent fingers of said individual for providing position signals, said recording media includes a memory and means are provided to encode said position signals in said memory.

10. The method of claim 7 wherein said at least one fingerprint comprises at least two fingerprints and including the step of positioning said at least two fingerprints at said input means in accordance with reference width and relative position data.

11. The method of claim 10 wherein said pre-recorded reflection hologram is a frequency multiplexed reflection hologram and wherein the step of illuminating an input means with incoherent light comprises illuminating with incoherent light having a frequency spectrum covering each frequency in said frequency multiplexed reflection hologram whereby the sensitivity of said fingerprint verification method to scale changes in said at least one reference fingerprint is reduced.

* * * * *